(12) United States Patent
Eisinger

(10) Patent No.: US 11,234,704 B2
(45) Date of Patent: Feb. 1, 2022

(54) CABLE-ACTUATED ADAPTER FOR SURGICAL STAPLING INSTRUMENT

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 141 days.

(21) Appl. No.: 16/807,393

(22) Filed: Mar. 3, 2020

(65) Prior Publication Data

US 2021/0275178 A1 Sep. 9, 2021

(51) Int. Cl.
*A61B 17/115* (2006.01)
*A61B 17/34* (2006.01)
*A61B 17/00* (2006.01)

(52) U.S. Cl.
CPC .......... *A61B 17/1155* (2013.01); *A61B 17/34* (2013.01); *A61B 2017/00398* (2013.01); *A61B 2017/00477* (2013.01)

(58) Field of Classification Search
CPC ................ A61B 17/1155; A61B 17/34; A61B 2017/00398; A61B 2017/00477
USPC ........................................... 227/175.1–182.1
See application file for complete search history.

(56) References Cited

U.S. PATENT DOCUMENTS

| | | | | |
|---|---|---|---|---|
| 4,671,445 | A * | 6/1987 | Barker | A61B 17/072 227/19 |
| 5,271,543 | A * | 12/1993 | Grant | A61B 17/115 227/179.1 |
| 7,303,106 | B2 | 12/2007 | Milliman et al. | |
| 9,724,100 | B2 * | 8/2017 | Scheib | A61B 17/1155 |
| 2005/0023325 | A1 * | 2/2005 | Gresham | A61B 17/115 227/176.1 |
| 2007/0023475 | A1 * | 2/2007 | Csiky | A61B 17/115 227/175.1 |
| 2012/0234890 | A1 * | 9/2012 | Aronhalt | A61B 17/068 227/175.1 |
| 2012/0265154 | A1 * | 10/2012 | Criscuolo | A61B 17/1155 604/258 |
| 2016/0374668 | A1 * | 12/2016 | Measamer | A61B 17/1155 227/175.1 |
| 2016/0374671 | A1 * | 12/2016 | Measamer | A61B 17/068 227/175.1 |

(Continued)

*Primary Examiner* — Robert F Long
(74) *Attorney, Agent, or Firm* — Carter, DeLuca & Farrell LLP

(57) ABSTRACT

A surgical stapling instrument includes an anvil assembly, a shell assembly, and an adapter assembly. The adapter assembly includes a tubular shaft, an approximation assembly, and a seal. The approximation assembly includes a lead screw, a tubular member, a cable, and a trocar assembly. The tubular member threadably engages the lead screw such that rotation of the lead screw causes axial displacement of the tubular member. The cable extends within the tubular shaft and is coupled to the tubular member for concomitant displacement with the tubular member. The trocar assembly extends from the cable. The trocar assembly is coupled to the anvil assembly such that axial displacement of the tubular member transitions the anvil assembly between a spaced apart configuration and an approximated configuration. The seal provides a fluid-tight seal such that the adapter assembly includes a sealed portion and an unsealed portion. The lead screw is disposed within the sealed portion.

15 Claims, 6 Drawing Sheets

(56) References Cited

U.S. PATENT DOCUMENTS

| | | | |
|---|---|---|---|
| 2016/0374673 A1* | 12/2016 | Stager | A61B 17/0644 227/176.1 |
| 2017/0128074 A1* | 5/2017 | Gutelius | A61B 17/1155 |
| 2017/0224346 A1* | 8/2017 | Sgroi | A61B 17/1155 |
| 2017/0333044 A1* | 11/2017 | Sgroi, Jr. | A61B 17/1155 |
| 2019/0090873 A1* | 3/2019 | Fox | A61B 17/1155 |
| 2019/0090874 A1* | 3/2019 | Fox | A61B 17/07207 |
| 2019/0090876 A1* | 3/2019 | Fox | A61B 17/1114 |
| 2019/0343517 A1 | 11/2019 | Zemlok et al. | |
| 2020/0015820 A1 | 1/2020 | Contini et al. | |

* cited by examiner

CABLE-ACTUATED ADAPTER FOR SURGICAL STAPLING INSTRUMENT

FIELD

The disclosure relates generally to surgical stapling instruments, and more particularly, to a cable-actuated adapter for surgical stapling instruments.

BACKGROUND

Anastomosis is the surgical joining of separate hollow organ sections. Typically, an anastomosis procedure follows surgery in which a diseased or defective section of hollow tissue is removed, and the end sections are stapled via a surgical stapling instrument. Depending on the desired anastomosis procedure, the end sections may be joined by circular or side-to-side organ reconstruction methods, for instance.

In a circular anastomosis procedure, the two ends of the organ sections are joined by means of a surgical stapling instrument which drives a circular array of staples through the end section of each organ section and simultaneously cores any tissue interior of the driven circular array of staples to free the tubular passage. Typically, these surgical stapling instruments include an elongated body portion having a handle portion at a proximal end to actuate the surgical stapling instrument and a staple holding component disposed at a distal end. An anvil assembly including an anvil retention rod with an attached anvil head is mounted to a trocar assembly at the distal end of the surgical stapling instrument adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are formed by the anvil head. An annular knife is advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a surgical stapling instrument for hemorrhoid treatment, the anvil head and the staple holding-component of the surgical stapling instrument are inserted through the anus and into the rectum with the anvil head and the staple-holding component in an open or spaced part position. Thereafter, a purse string suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly is engaged with the anvil retention rod. The surgical stapling instrument is fired to remove the hemorrhoidal tissue and staple the tissue.

SUMMARY

In accordance with the disclosure, a surgical stapling instrument includes an anvil assembly, a shell assembly, and an adapter assembly. The anvil assembly includes an anvil head and an anvil center rod extending proximally from the anvil head. The shell assembly includes an annular staple cartridge including a plurality of staples. The adapter assembly includes a tubular shaft, an approximation assembly, and a seal. The tubular shaft supports the shell assembly at a distal portion of the tubular shaft. The approximation assembly includes a lead screw, a tubular member, a cable, and a trocar assembly. The tubular member threadably engages the lead screw such that rotation of the lead screw causes axial displacement of the tubular member. The cable extends within the tubular shaft and is coupled to the tubular member for concomitant displacement with the tubular member. The trocar assembly extends from the cable. The trocar assembly is coupled to the anvil assembly such that axial displacement of the tubular member transitions the anvil assembly between a spaced apart configuration, in which, the anvil head is spaced apart from the annular staple cartridge, and an approximated configuration, in which, the anvil head is in juxtaposed alignment with the annular staple cartridge. The seal provides a fluid-tight seal such that the adapter assembly includes a sealed portion and an unsealed portion. The lead screw is disposed within the sealed portion.

In an aspect, the cable may be formed of a flexible material.

In another aspect, the cable may be configured for flexion in a radial or an axial direction.

In yet another aspect, the seal of the adapter assembly may engage the cable in a sealing relation.

In an aspect, the lead screw may be disposed proximal of the seal.

In another aspect, the lead screw may include a lubricant to enhance engagement with the tubular member of the approximation assembly.

In yet another aspect, the trocar assembly may be attachable to the cable.

In still yet another aspect, the trocar assembly may include a connecting member secured to the cable, and a trocar extending distally from the connecting member and engageable with the anvil center rod of the anvil assembly.

In still yet another aspect, the trocar may be releasably coupled to the connecting member.

In an aspect, the anvil center rod may include a plurality of resilient fingers defining a longitudinal bore. The trocar may be releasably received in the longitudinal bore.

In another aspect, the cable may have a diameter of about 0.25 inch.

In yet another aspect, the shell assembly may be releasably coupled to the distal portion of the tubular shaft.

In still yet another aspect, the surgical stapling instrument may further include a handle assembly. The adapter assembly may include an interface portion attachable to the handle assembly of the surgical stapling device.

In still yet another aspect, the sealed portion of the adapter assembly may be adjacent the interface portion.

In still yet another aspect, the tubular shaft may have a bend.

In accordance with the disclosure, an adapter assembly for use with a surgical stapling instrument includes a tubular shaft and an approximation assembly. The tubular shaft supports a shell assembly including an annular staple cartridge. The approximation assembly includes a tubular member defining a lumen therethrough, a lead screw threadably received in the lumen of the tubular member such that rotation of the lead screw causes axial displacement of the tubular member, a flexible cable extending from the tubular member for concomitant displacement therewith, a trocar assembly coupled to the cable, and a seal. The trocar assembly is attachable to an anvil assembly and movable between a retracted position and an advanced position. The seal is supported on the tubular shaft to seal the lead screw from fluid.

BRIEF DESCRIPTION OF DRAWINGS

An adapter assembly for use with a surgical stapling instrument is disclosed herein with reference to the drawings, wherein.

DETAILED DESCRIPTION

Figure 1:
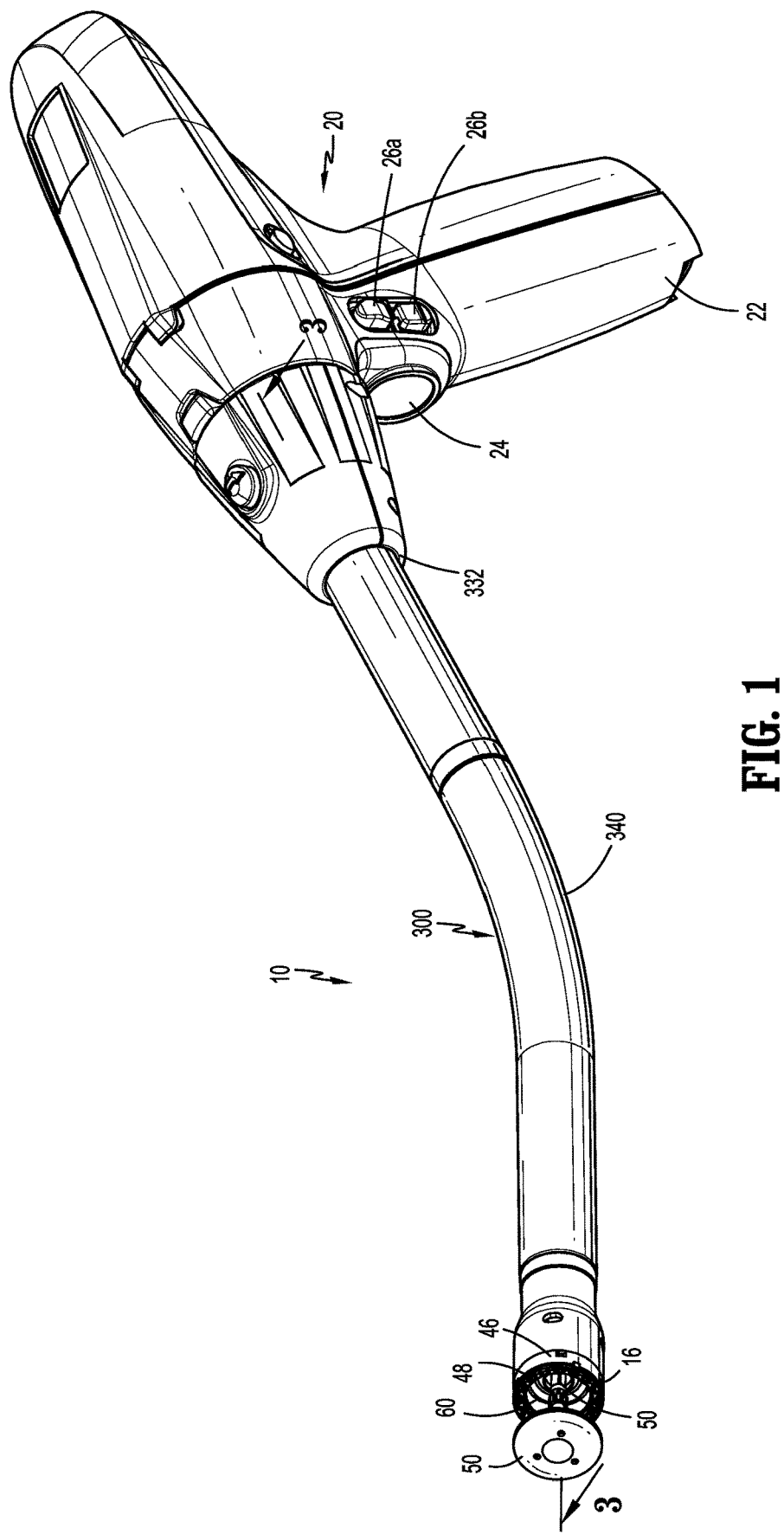
FIG. 1 is a perspective view of a surgical stapling instrument in accordance with the disclosure.

A surgical stapling instrument is described in detail with reference to the drawings, wherein like reference numerals designate corresponding elements in each of the several views. As used herein, the term "distal" refers to that portion of the instrument, or component thereof which is farther from the user during customary use of the instrument while the term "proximal" refers to that portion of the instrument or component thereof which is closer to the user during customary use of the instrument.

Figure 2:
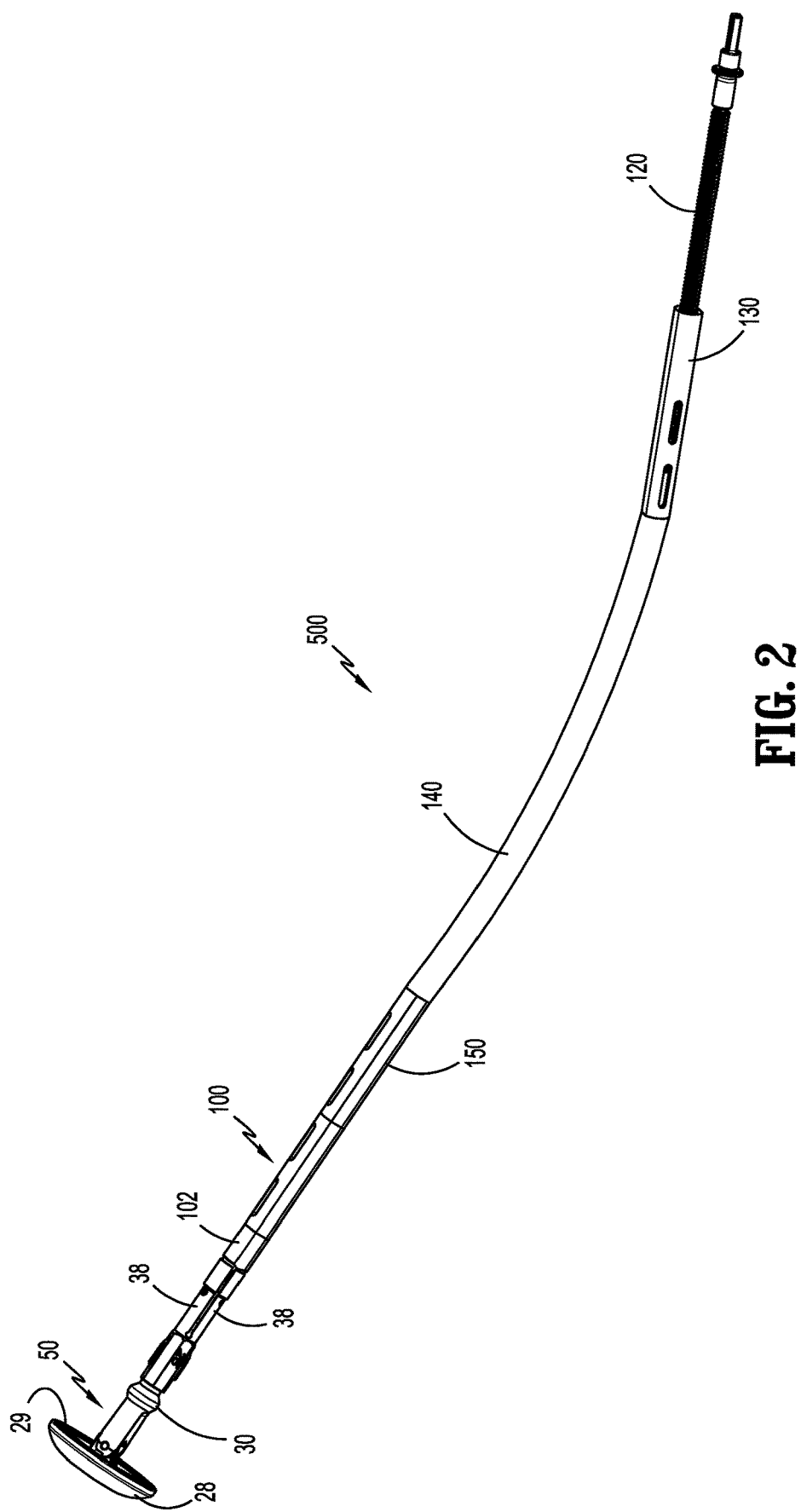
FIG. 2 is a perspective view of an approximation assembly of the surgical stapling instrument of FIG. 1.

With reference to FIGS. 1 and 2, an approximation assembly for use with a surgical instrument, in the form of a surgical stapling instrument 10 is shown generally as 500. The approximation assembly 500 enables placement of lubricated components thereof in a fluid-tight sealed manner such that the lubricated components are protected from cleaning fluids during, e.g., reprocessing, of the surgical stapling instrument 10. The surgical stapling instrument 10 is a circular stapling instrument including a handle assembly 20, an adapter assembly 300 extending distally from the handle assembly 20, a shell assembly 16 supported on a distal portion of the adapter assembly 300, and an anvil assembly 50 operatively coupled to the handle assembly 20.

The handle assembly 20 is illustrated as a powered assembly and includes a stationary grip 22, actuation button 24 for controlling firing of staples (not shown) from an annular staple cartridge 48 of the shell assembly 16, and approximation buttons 26a, 26b for controlling axial displacement of the anvil assembly 50 towards and away from the shell assembly 16. For a detailed description of the structure and function of exemplary powered handle assemblies, reference may be made to U.S. Patent Application Publication Nos. 2020/0015820 and 2019/0343517, the entire contents of which are incorporated herein by reference. Although the disclosure illustrates a powered assembly, it is envisioned that the advantages of the disclosure as described in detail below are also applicable to surgical stapling instruments having manually operated handle and body assemblies or robotically actuated surgical instruments. U.S. Pat. No. 7,303,106 (the '106 Patent) discloses an example of a surgical stapling instrument including a manually actuated handle assembly and is incorporated herein by reference in its entirety. It is also envisioned that the disclosed stapling instrument can be supported on a robotic system and need not include a handle assembly.

With continued reference to FIGS. 1 and 2, the adapter assembly 300 includes an interface portion 332 detachably coupled to the handle assembly 20, a tubular shaft 340 extending distally from the interface portion 332, and the approximation assembly 500 movably supported within the adapter assembly 300. The shell assembly 16 is supported on a distal portion of the tubular shaft 340 and includes a shell housing 46 and an annular staple cartridge 48 that defines annular rows of staple receiving pockets 50. In particular, the shell assembly 16 may be releasably coupled to the distal portion of the tubular shaft 340 to facilitate replacement of the annular staple cartridge 48 after each use.

Each of the staple receiving pockets 50 supports a staple (not shown) that can be fired from the annular staple cartridge 48 via actuation of the actuation button 24 of the handle assembly 20 and formed within the staple forming pockets (not shown) of a staple forming surface 29 of an anvil head 28 of the anvil assembly 50. The shell housing 46 of the shell assembly 16 defines an annular cavity 60. The annular cavity 60 supports a staple pusher (not shown) and an annular knife (not shown) such that the staple pusher and the annular knife are movable in relation to the annular staple cartridge 48 to eject the staples from the annular staple cartridge 48 and to dissect or cut tissue positioned within an annulus defined by the annular staple cartridge 48. For a detailed description of the structure and function of the exemplary shell assemblies reference may be made to the '106 Patent, the entire contents of each of which are incorporated herein by reference.

With particular reference to FIG. 2, the anvil assembly 50 includes an anvil head 28 and an anvil center rod 30. The anvil head 28 includes the staple deforming surface 29 that includes staple deforming pockets (not shown). The anvil center rod 30 includes a plurality of resilient fingers 38 defining a longitudinal bore that is dimensioned to receive and releasably engage a trocar 102 of the trocar assembly 100. In an aspect, the anvil head 28 may be pivotally coupled to the anvil center rod 30 and may be movable between an operative position for forming staples and a tilted, reduced profile position.

Figure 3:
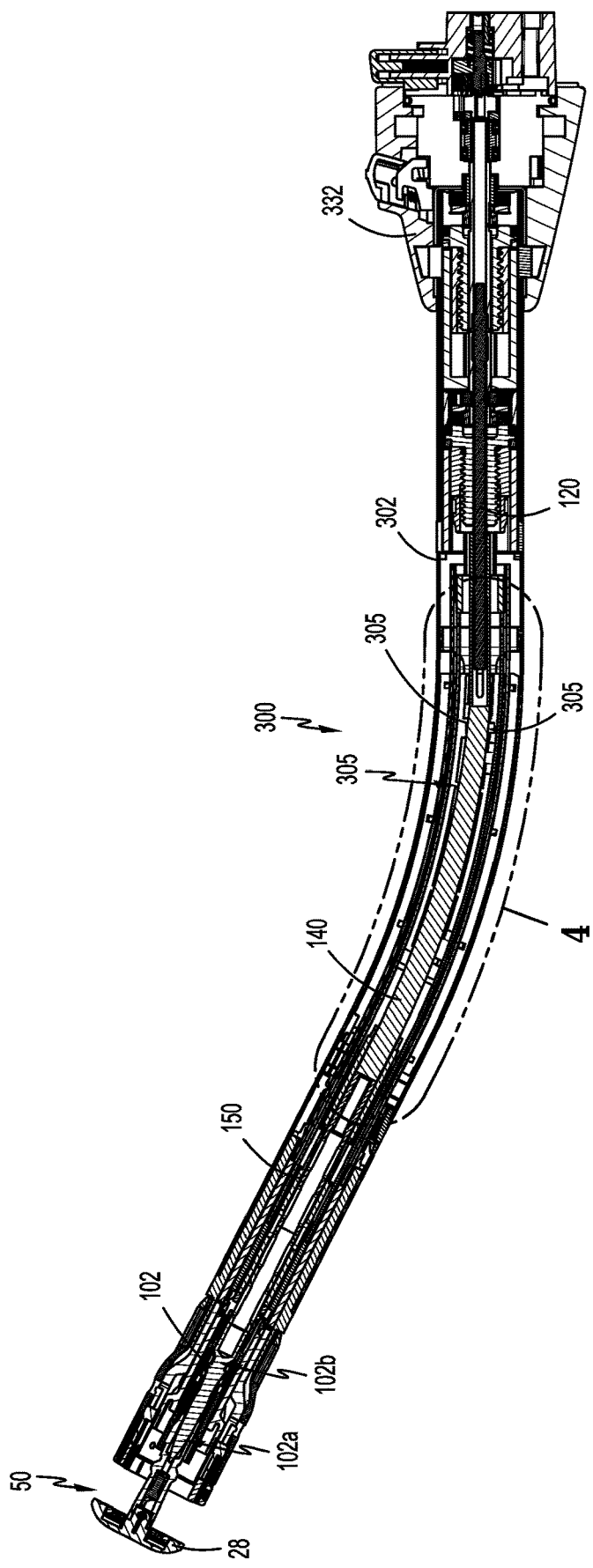
FIG. 3 is cross-sectional view of the surgical stapling instrument of FIG. 1 cut along section line 3-3 of FIG. 1.
Figure 4:
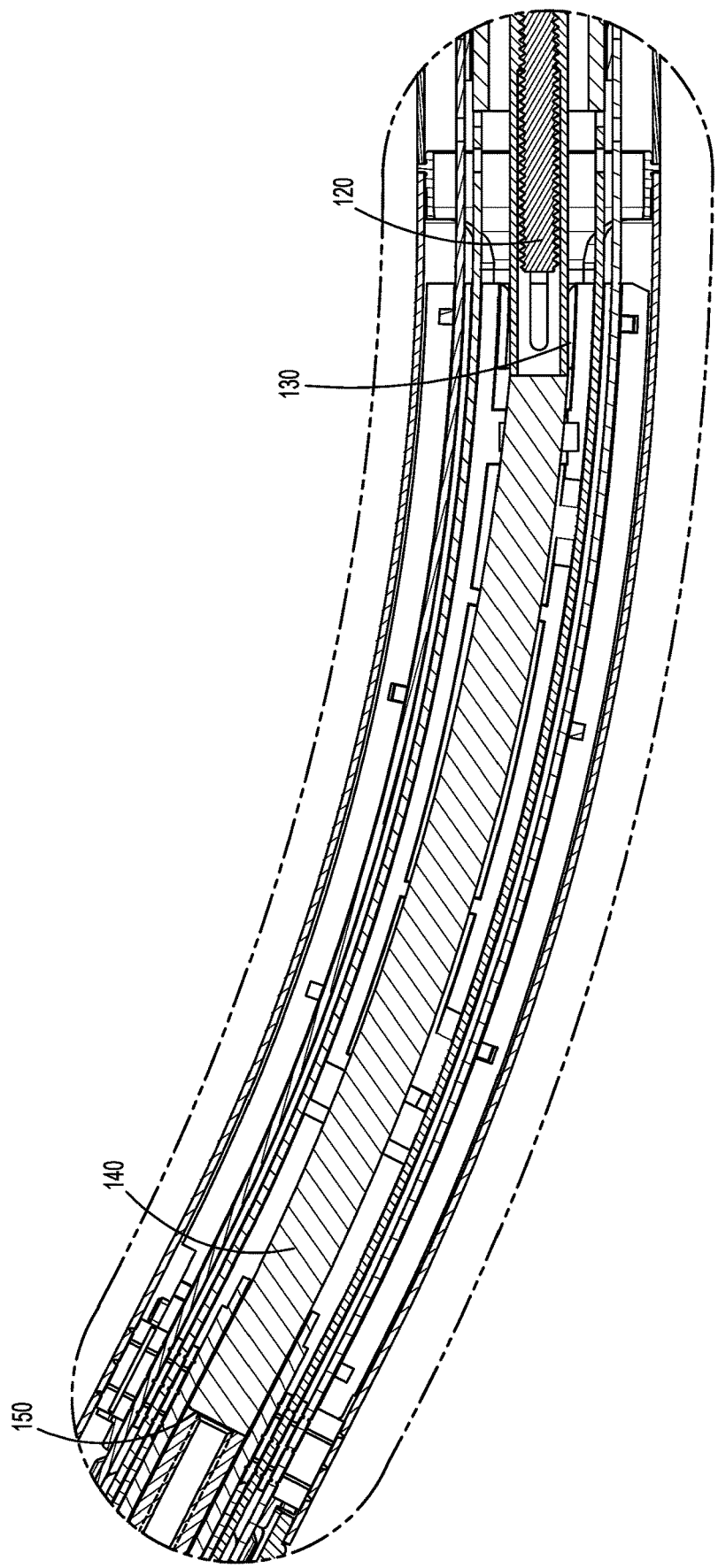
FIG. 4 is an enlarged cross-sectional view of the indicated area of detail of FIG. 3.

With reference to FIGS. 2 and 3, the approximation assembly 500 includes a lead screw 120, a tubular member 130 threadably coupled to the lead screw 120, a cable 140 that is connected to the tubular member 130, and the trocar assembly 100 that is coupled to the cable 140. The anvil assembly 50 may be releasably coupled to the approximation assembly 500 for concomitant axial displacement of the anvil assembly 50 relative to the shell assembly 16 (FIG. 1) by activating an actuator (not shown) such as, e.g., an electric motor, in the handle assembly 20 (FIG. 1). The lead screw 120 is operatively coupled to the actuator of the handle assembly 20 for rotational input. The lead screw 120 is rotatably slidable within the tubular member 130 such that rotation of the lead screw 120 causes axial displacement of the tubular member 130.

The cable 140 is attached to the tubular member 130 such that axial displacement of the tubular member 130 is imparted to the cable 140. In an aspect, the cable 140 may have a diameter of about 0.25 inch. In particular, the cable 140 may be formed of a flexible material to enable flexion of the cable 140 in, e.g., radial and/or axial, directions. In this manner, the cable 140 may accommodate the shape and contour of the adapter assembly 300. In addition, the flexibility of the cable 140 enables placement of the lead screw 120 in a proximal portion 302 (FIG. 1) of the adapter assembly 300, e.g., adjacent the interface portion 332. Furthermore, the cable 140 enables placement of the lead screw 120 in a portion or compartment that is sealed from fluid. For example, the lead screw 120 may be placed in the proximal portion 302 of the adapter assembly 300 that is sealed from fluid. Under such a configuration, any lubricant or grease that is applied to the lead screw 120 may be protected from, e.g., the cleaning fluid, used in reprocessing or sterilization of the adapter assembly 300, which may enhance reusability and performance of the adapter assembly 300. For example, the adapter assembly 300 may include seals 305 in a fluid-tight sealing relation with the cable 140. In addition, other components such as, e.g., a strain gauge 70, that measures the strain in the adapter assembly 300 during movement of the anvil assembly 50 in relation to the staple cartridge 48 to identify if the anvil assembly 50 is properly coupled to the trocar assembly 100, may also be positioned within the sealed proximal portion 302.

Figure 5:
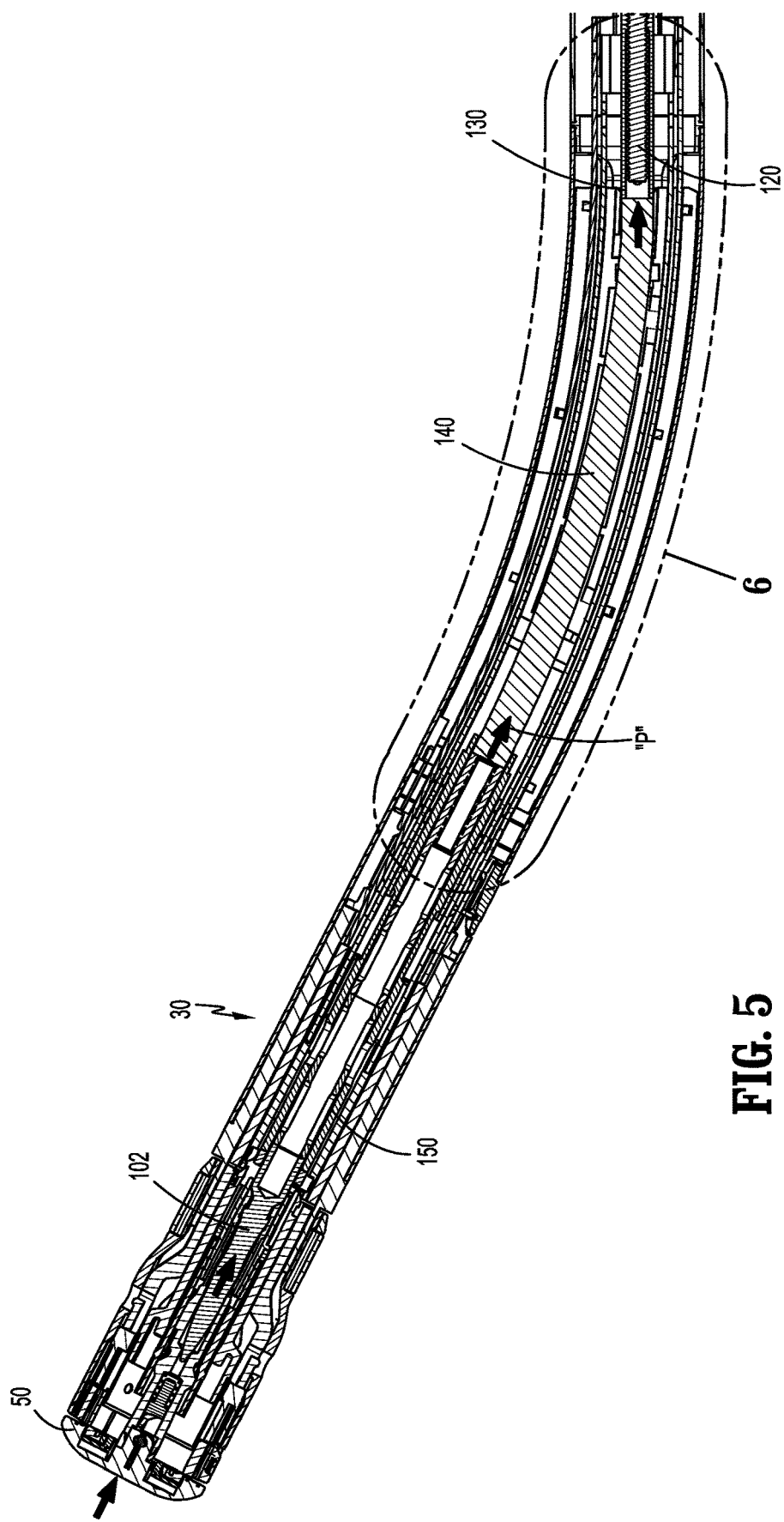
FIG. 5 is a cross-sectional view of the adapter assembly and the anvil assembly of the surgical stapling instrument of FIG. 3, illustrating the adapter assembly when the anvil assembly is in an approximated configuration.
Figure 6:
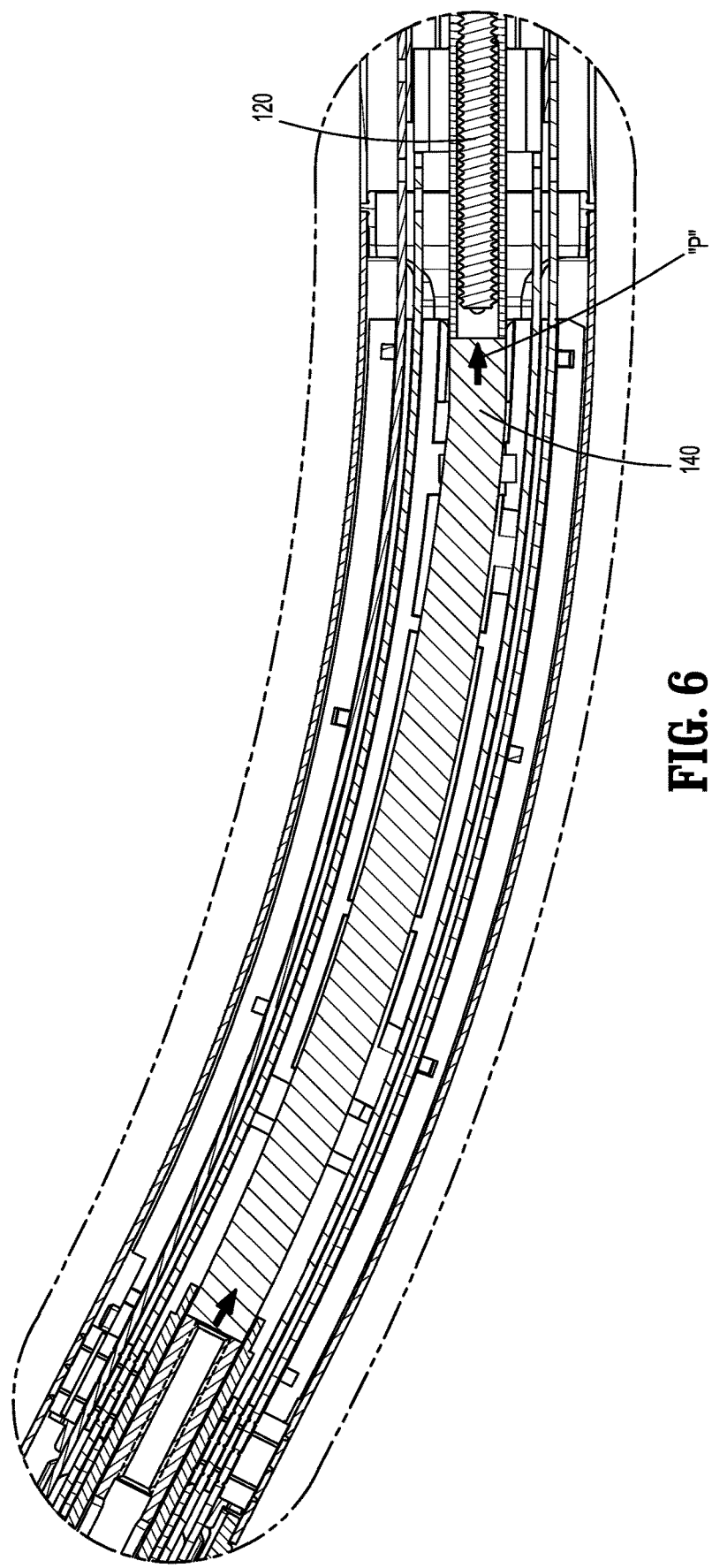
FIG. 6 is an enlarged cross-sectional view of the indicated area of detail of FIG. 5.

With reference to FIGS. 2 and 3, the connecting member 150 extends distally from the cable 140. The trocar 102 includes a distal portion 102a that is tapered and a proximal portion 102b that is larger than the distal portion 102a. The distal portion 102a is detachably received within the longitudinal bore that is defined by the plurality resilient fingers 38 of the anvil assembly 50, and the proximal portion 102b is, e.g., detachably, coupled to the connecting member 150. In an aspect, it is contemplated that the trocar 102 may be fixed with the connecting member 150. Under such a configuration, rotational output of the actuator of the handle assembly 20 provides rotational input to the lead screw 120, which, in turn, causes axial displacement of the tubular member 130. Displacement of the tubular member 130 imparts concomitant displacement to the cable 140, which, in turn, transitions the anvil assembly 50 between a spaced apart configuration (FIG. 3) and an approximated configuration (FIG. 5), in which, the staple deforming surface 29 of the anvil assembly 50 is in juxtaposed alignment with the annular staple cartridge 48.

Initially, tubular tissue may be placed between the anvil head 28 and the shell assembly 16 to perform anastomosis. At this time, the surgical stapling instrument 10 may be in the spaced apart configuration (FIG. 3). The approximation button 26a may be pressed to transition the anvil head 28 of the anvil assembly 50 to the approximated configuration (FIG. 5) to clamp tissue between the anvil head 28 and the annular cartridge assembly 48. At this time, the actuator of the handle assembly is activated to provide rotational input to the lead screw 120. Rotation of the lead screw 120 provides axial displacement of the cable 140 in the direction of arrows "P" (FIG. 5), which, in turn, retracts the anvil head 28 to the approximated configuration. At this time, tissue is clamped between the anvil head 28 and the shell assembly 16. Thereafter, the actuation button 24 may be pressed to activate an actuator to perform stapling and cutting of tissue disposed between the anvil head 28 and the shell assembly 16. Thereafter, the clinician may press the approximation button 26b to transition the anvil head 28 to the spaced apart configuration. After the surgical procedure, the adapter assembly 300 may be reprocessed or sterilized for reuse. The anvil assembly 50 may be detached from the trocar assembly 100 and/or the trocar 102 may be detached from the connecting member 150 of the trocar assembly 100 prior to reprocessing or sterilization.

Persons skilled in the art will understand that the instruments and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical stapling instrument comprising:
    an anvil assembly including an anvil head and an anvil center rod extending proximally from the anvil head;
    a shell assembly including an annular staple cartridge including a plurality of staples; and
    an adapter assembly including:
        a tubular shaft supporting the shell assembly at a distal portion of the tubular shaft;
        an approximation assembly including:
            a lead screw;
            a tubular member threadably engaging the lead screw such that rotation of the lead screw causes axial displacement of the tubular member;
            a cable extending within the tubular shaft and coupled to the tubular member for concomitant displacement with the tubular member; and
            a trocar assembly extending from the cable, the trocar assembly coupled to the anvil assembly such that axial displacement of the tubular member transitions the anvil assembly between a spaced apart configuration, in which, the anvil head is spaced apart from the annular staple cartridge, and an approximated configuration, in which, the anvil head is in juxtaposed alignment with the annular staple cartridge; and
        a seal providing a fluid-tight seal such that the adapter assembly includes a sealed portion and an unsealed portion, wherein the lead screw is disposed within the sealed portion.

2. The surgical stapling instrument according to claim 1, wherein the cable is formed of a flexible material.

3. The surgical stapling instrument according to claim 1, wherein the cable is configured for flexion in a radial or an axial direction.

4. The surgical stapling instrument according to claim 1, wherein the seal of the adapter assembly engages the cable in a sealing relation.

5. The surgical stapling instrument according to claim 1, wherein the lead screw is disposed proximal of the seal.

6. The surgical stapling instrument according to claim 1, wherein the lead screw includes a lubricant to enhance engagement with the tubular member of the approximation assembly.

7. The surgical stapling instrument according to claim 1, wherein the trocar assembly is attachable to the cable.

8. The surgical stapling instrument according to claim 1, wherein the trocar assembly includes a connecting member secured to the cable, and a trocar extending distally from the connecting member and engageable with the anvil center rod of the anvil assembly.

9. The surgical stapling instrument according to claim 1, wherein the trocar is releasably coupled to the connecting member.

10. The surgical stapling instrument according to claim 8, wherein the anvil center rod includes a plurality of resilient fingers defining a longitudinal bore, the trocar releasably received in the longitudinal bore.

11. The surgical stapling instrument according to claim 1, wherein the cable has a diameter of about 0.25 inch.

12. The surgical stapling instrument according to claim 1, wherein the shell assembly is releasably coupled to the distal portion of the tubular shaft.

13. The surgical stapling instrument according to claim 1, further comprising a handle assembly, the adapter assembly including an interface portion attachable to the handle assembly of the surgical stapling device.

14. The surgical stapling instrument according to claim 13, wherein the sealed portion of the adapter assembly is adjacent the interface portion.

15. The surgical stapling instrument according to claim 1, wherein the tubular shaft has a bend.

* * * * *